United States Patent [19]

Schweitzer et al.

[11] Patent Number: 5,047,208
[45] Date of Patent: Sep. 10, 1991

[54] BLOOD GAS MONITORING SENSORS

[75] Inventors: Jeffrey A. Schweitzer, St. Anthony; Keith J. Proctor, Lino Lakes, both of Minn.

[73] Assignee: Medtronic, Inc., Minneapolis, Minn.

[21] Appl. No.: 314,615

[22] Filed: Feb. 23, 1989

[51] Int. Cl.[5] .......................................... G01N 21/27
[52] U.S. Cl. ..................................... 422/58; 128/634;
356/39; 356/412; 422/57; 422/82.06; 436/68;
436/133; 385/27; 385/50
[58] Field of Search ............. 422/57, 58, 82.06, 82.07,
422/82.08; 128/634; 356/39, 412; 436/68, 133;
350/96.29

[56] References Cited

U.S. PATENT DOCUMENTS

| 3,904,373 | 9/1975 | Harper | 422/57 |
| 4,682,895 | 7/1987 | Costello | 422/82.06 X |
| 4,706,677 | 11/1987 | Goorsky et al. | 128/634 |
| 4,758,298 | 7/1988 | Goorsky et al. | 156/296 |
| 4,785,814 | 11/1988 | Kane | 128/634 |
| 4,800,886 | 1/1989 | Nestor | 128/634 |
| 4,919,891 | 4/1990 | Yafuso et al. | 422/82.08 X |

OTHER PUBLICATIONS

Article entitled, "Fiber-Optice Sensors for Biomedical Applications", by John I Paterson et al., published in *Science*, 13 Apr. 1984, pp. 123-127.

*Primary Examiner*—Jill Johnston

[57] ABSTRACT

Colorimetric, fiber optic sensors for measuring pH, $PCO_2$ and/or other chemical parameters of the blood. The sensors are fabricated using a single optical fiber, which is provided with a chamber at its distal end containing a pH sensitive dye. Located distal to the chamber is a white reflective surface located within 0.04" from the end of the optical fiber, which enhances the performance of the sensor.

14 Claims, 3 Drawing Sheets

BLOOD GAS MONITORING SENSORS

CROSS REFERENCE TO COMMONLY ASSIGNED, CO-PENDING APPLICATION

Reference is made to U.S. patent application Ser. No. 07/314561 for a "POLYMER DYE FOR FIBER OPTIC SENSOR" by Fogt et al, filed Feb. 23, 1989, now U.S. Pat. No. 4,906,249.

BACKGROUND OF THE INVENTION

This invention relates generally to blood gas monitoring, and more particularly to fiber optic reflectance sensors.

Early designs of fiber optic pH and $CO_2$ sensors were done by Peterson, as described in the article "FIBER OPTIC PH PROBE FOR PHYSIOLOGICAL USE", by Peterson et al, published in *Analytical Chemistry*, Vol. 52, pp. 864-869, 1980 and by Vurek, as disclosed in the article "A FIBER OPTIC PCO2 SENSOR", by Vurek et al, published in *Annals of Biomedical Engineering*, Vol. 11, pp. 499-510, 1983. The pH sensor, described by Peterson, employed two optical fibers, connected to a semipermeable membrane pouch filled with phenol red dye bonded to a polyacrylamide powder substrate and mixed with reflective glass microspheres. The Vurek sensor employs the same dye (phenol red) in a bicarbonate buffer solution encased by a gas permeable, ion impermeable membrane. As carbon dioxide passes through the membrane, the pH of the buffer solution is altered.

In both the Peterson and Vurek sensors, the light absorption properties of phenol red are utilized in order to produce a color change, which can be monitored optically. Phenol red is a weakly ionizing acid which disassociates into an acid form having an absorption peak at 430 nm and a base form having an absorption peak at 560 nm. The proportions of acid and base forms are determined by the pH of the solution. Therefore, the pH of the solution containing phenol red can be monitored using light from a green LED, preferably having a frequency band centered at about 560 nm. In both sensors, the green light is provided to the sensor capsule by means of one of the optical fibers, and reflected light is monitored using the second optical fiber.

Recently, single optical fiber sensors employing fluorescence based dye systems have been introduced, as described in "OPTICAL FLUORESCENCE AND ITS APPLICATION TO AN INTRAVASCULAR BLOOD GAS MONITORING SYSTEM", by Gehrich et al, published in *IEEE Transactions on Biomedical Engineering*, Vol. BME-33, No. 2, pp. 117-132, 1986. This article is incorporated herein by reference in its entirety.

SUMMARY OF THE INVENTION

The present invention provides a single fiber colorimetric optical sensor for sensing chemical parameters of the blood. In the two disclosed embodiments, it is configured as pH and $PCO_2$ sensors, and employs dye systems based on phenol red. In conjunction with both sensors, the absorption of green light having a wavelength band centered at approximately 560 nm is measured. In use, the sensor is coupled to a monitoring apparatus which includes one or more light sources and a light measuring apparatus. The optical fiber carries light from the light source to the sensor and reflected light from the sensor back to the apparatus for measuring light intensity.

The sensor is provided with a dye chamber containing a colorimetric dye, typically phenol red. The dye is located between the end of the optical fiber and a reflective surface, perpendicular to the axis of the optical fiber. This configuration allows the construction of a single fiber colorimetric sensor, having adequate characteristics for use in an vivo blood gas monitoring. Moreover, this structure allows for simple and economical sensor fabrication.

DETAILED DESCRIPTION OF THE INVENTION

Figure 1:
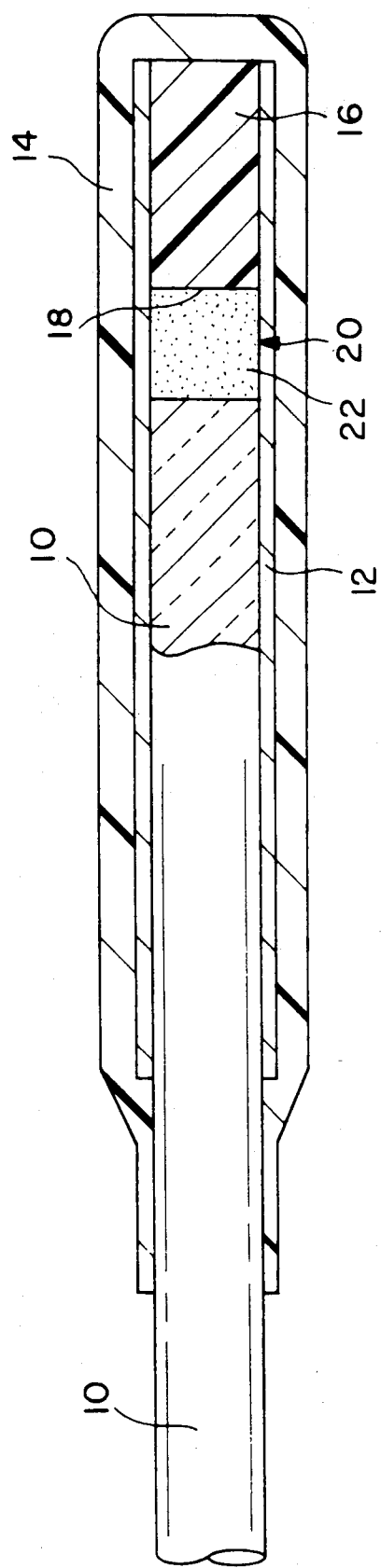
FIG. 1 shows a side, cutaway view of a $CO_2$ sensor according to the present invention.

FIG. 1 shows a side, cutaway view of a $PCO_2$ sensor according to the present invention. The sensor assembly is mounted at the distal end of an optical fiber 10, which is adapted to be coupled to light generating and measuring equipment, such as that disclosed in the above cited Gehrich et al article. Surrounding the distal end of the optical fiber 10 is a cellulosic semipermeable membrane of the type typically used for dialysis tubing. Sealing the distal end of the membrane 12 is a plug of titanium dioxide impregnated epoxy 16. The addition of titanium dioxide to the epoxy provides a white color to allow the proximal surface 18 to function as a reflective surface, reflecting light emitted from the distal end of optical fiber 10. Alternatively, other reflective surfaces, such as miniature mirrors or metallized layers, might be used. However, the construction illustrated is both economical and readily produced.

The distal end of optical fiber 10, the proximal end of plug 16, and membrane 12 together define the outer boundaries of the dye chamber 20. Dye chamber 20 is filled with an aqueous mixture of sodium bicarbonate and sodium chloride along with a small amount of phenol red. Particular proportions which have been successfully used are: $0.030M$ $NaHCO_3 + 0.12M$ $NaCl + 0.5$ g/liter phenol red.

Surrounding membrane 12 is a layer of silicone rubber 14, which functions as a gas permeable membrane. In alternative embodiments, membrane 12 may be omitted, and silicone rubber 14 used as the only membrane. Because silicone rubber will allow water vapor to pass through, the sensor can be built dry, and hydrated at a later time.

$CO_2$ dissolved in the fluid to be measured passes through silicone rubber 14 and membrane 12, altering the pH of the dye mixture 22 in chamber 20. Light emitted from the distal end of fiber 10 passes through dye mixture 22, and is reflected off of reflective surface 18. Depending upon the pH of the dye mixture, the amount of light absorbed in the measuring chamber 20 will vary. Measurement of the reflected light thus provides a measurement of $PCO_2$ of the fluid in which the sensor is located. Reflective surface 18 is preferably generally perpendicular to the axis of optical fiber 10, and should be spaced no more than about 0.004" from the end of optical fiber 10, in order to function with adequate efficiency.

Figure 2:
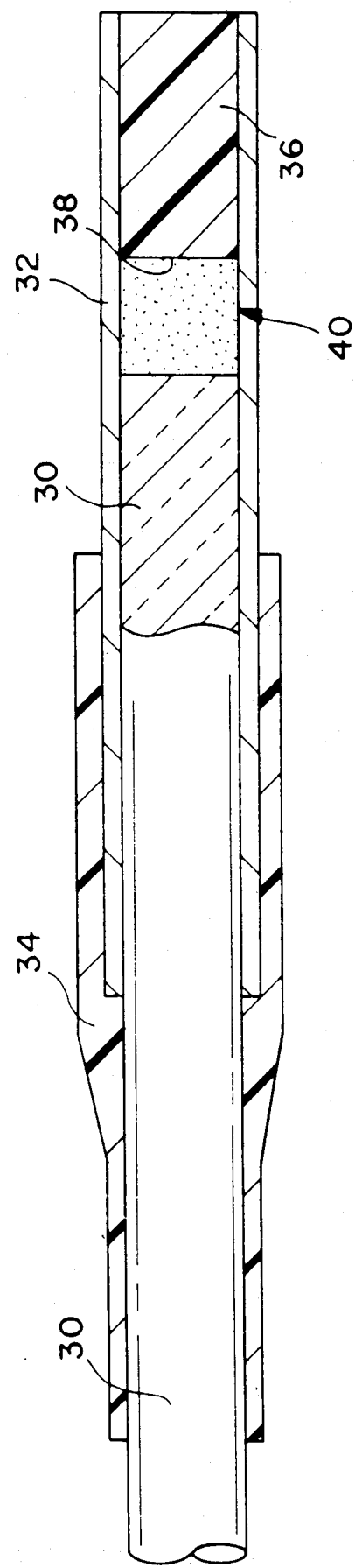
FIG. 2 shows a side, cutaway view of a pH sensor according to the present invention.

FIG. 2 is a side, cutaway view of a sensor according to the present invention configured as a pH sensor. The sensor assembly is mounted at the distal end of an optical fiber 30, similar to that discussed above in conjunction with the sensor illustrated in FIG. 1. Surrounding the optical fiber 30 is a semipermeable membrane 32, which may be a cellulosic membrane of the type typically used as dialysis tubing. Binding the membrane 32 to the optical fiber 30 is adhesive 34, which may be a UV curing epoxy. An epoxy plug 36 is located at the distal end of the sensor. Like plug 16 discussed above, it is white in color, and its proximal surface 38 serves as a reflector for light emitted by optical fiber 30.

Dye chamber 40 is filled with a pH indicating dye, phenol red, bound to a polymeric composition including substantially equal relative amounts of anionic and cationic monomer constituents, along with minor amounts of neutral monomer constituents. These constituents are copolymerized together in the presence of the dye. The anionic monomer constituent may be the sodium salt of 2-acrylamido-2-methyl propane sulfonic acid (Na AMPS), the cationic monomer constituent may be methylacrylamidopropyl-trimethylamoninium chloride (MAPTAC), and the neutral monomer constituent may be acrylamide. One appropriate ratio of cationic: anionic: neutral monomers is 2:2:1 by weight. This dye composition is discussed in more detail in U.S. patent application Ser. No. 07/314561 for a "POLYMER DYE FOR FIBER OPTIC SENSOR" filed on the date of this application, by Fogt et al, and now U.S. Pat. No. 4,906,249, incorporated herein by reference in its entirety.

As discussed in conjunction with the sensor illustrated in FIG. 1, the distance between the end of optical fiber 30 and the proximal surface 38 of plug 36 should be no more than about 0.004", in order to assure adequate reflection of light from fiber 30. As discussed above, other reflective surfaces, such as mirrors or metallized surfaces could be substituted for the white epoxy plug 36.

Figure 3:
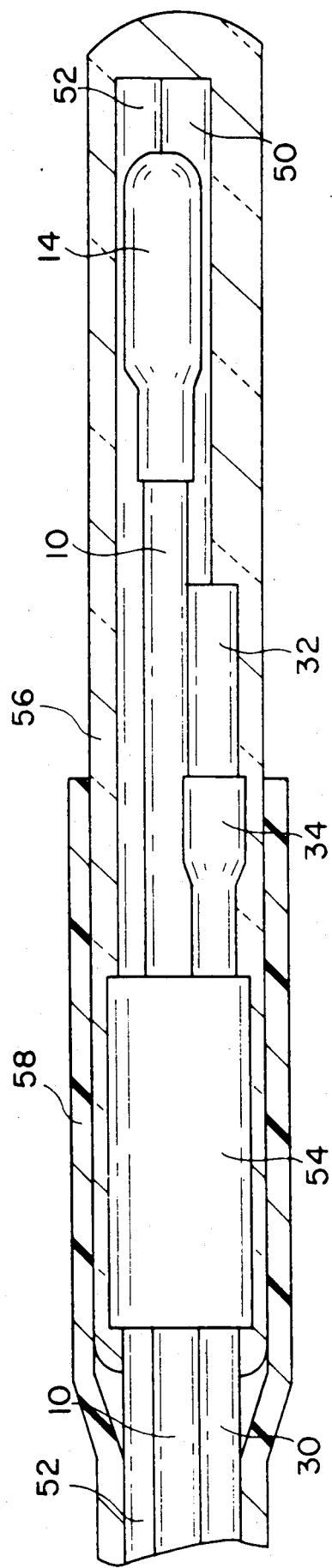
FIG. 3 shows a side, cutaway view of an assembled multisensor probe, employing the pH and $PCO_2$ sensors illustrated in FIGS. 1 and 2, along with two additional optical fibers which function as a reflectance oximeter.

FIG. 3 shows a cutaway view of the sensors illustrated in FIGS. 1 and 2 assembled in the form of a multisensor lead. The pH sensors of FIGS. 1 and 2, mounted to optical fibers 10 and 30, respectively, are bundled with two additional optical fibers 50 and 52, which function as a reflectance oximeter. The fibers are held in alignment with one another by means of an epoxy adhesive 54. The end of the fiber bundle is coated with a hydrophylic, gas permeable polymer 56, which allows for free passage of dissolved ions and gases from body fluid, to the pH and $PCO_2$ sensors. Polymeric coating 56 may be a hydrophylic polyurethane sold under the trade designation BPS 533, by Thoratec, Inc., California. In its preferred embodiment, polymer coating 56 is provided with a covalently bound heparin coating, applied to the polymeric coating as set forth in U.S. Pat. No. 4,613,665 issued to Olle Larm for a "PROCESS FOR COVALENT COUPLING FOR THE PRODUCTION OF CONJUGATES, AND POLYSACCHARIDE CONTAINING PRODUCTS THEREBY OBTAINED". This patent is incorporated by reference in its entirety. The bundled optical fibers are covered by a tubular sheath 58, which may be formed of heat shrink plastic, and shrunk down over the fibers. Sheath 58 extends to the proximal end of the sensor lead assembly.

In conjunction with the above description, we claim:

1. Colorimetric sensor for measurement of the amount of a chemical constituent dissolved in a fluid, comprising:
   a chamber containing a colorimetric dye means for changing light absorption characteristics in response to changes in the amount of said chemical constituent, for indicating the amount of said chemical constituent;
   fiber optic means having a proximal end and a distal end for delivering light from the light source to said chamber and for carrying light reflected from said chamber to a means for monitoring light intensity, the distal end of said fiber optic means coupled to said chamber and exposed to said colorimetric dye means; and
   reflective means distal to said dye means for reflecting light delivered to said chamber by said fiber optic means, said reflective means comprising a white reflective surface, perpendicular to the axis of said fiber optic means and spaced no more than about 0.004" from the distal end of said fiber optic means.

2. A sensor as in claim 1 wherein said chemical constituent comprises the pH of said fluid, and wherein said colorimetric dye means changes light absorption characteristics in response to changes to pH of said fluid.

3. A sensor according to claim 1 wherein said chemical constituent comprises dissolved carbon dioxide, and wherein said colorimetric dye means changes absorption characteristics in response to changes in the amount of dissolved carbon dioxide in said fluid.

4. A sensor according to claim 1 wherein said chamber further comprises a wall permeable to said fluid.

5. A sensor according to claim 1 or claim 2 wherein said chamber further comprises a fluid permeable outer wall, impermeable to said colorimetric dye means.

6. A sensor according to claim 1 or claim 2 wherein said chamber further comprises an outer wall permeable to said chemical constituent, but impermeable to said colorimetric dye means.

7. A sensor according to claim 1 wherein said fiber optic means comprises a single optical fiber.

8. A sensor according to claim 7 wherein said chamber of said sensor comprises a tubular semipermeable membrane, mounted around the end of said optical fiber, and wherein said reflective surface of said reflective means is mounted within the distal end of said tubular membrane, distal to said colorimetric dye means.

9. A sensor according to claim 1 wherein said reflective means comprises an epoxy base adhesive with titanium dioxide as a coloring agent.

10. A sensor according to claim 1 or claim 2 wherein said colorimetric dye means comprises phenol red bound to a polymeric substrate, and wherein said dye chamber comprises a fluid permeable outer wall.

11. A sensor according to claim 1 or claim 3 wherein said colorimetric dye means comprises phenol red dissolved in a solution of sodium bicarbonate, and wherein said chamber comprises an outer wall permeable to dissolve gases including carbon dioxide, but impermeable to the dissolved ionic substances.

12. Colorimetric sensor for measurement of the amount of a chemical constituent dissolved in a fluid, comprising:
    a chamber containing a colorimetric dye means for changing light absorption characteristics in response to changes in the amount of said chemical constituent, said chamber comprising a tubular semipermeable membrane having a proximal end and a distal end and containing said colorimetric dye means;

fiber optic means having a proximal end and a distal end for delivering light from the light source to said chamber and for carrying light reflected from said chamber to a means for monitoring light intensity, the distal end of said fiber optic means located within said tubular membrane and sealed to said tubular membrane, the distal end of said fiber optic means exposed to said colorimetric dye means; and a plug of reflective adhesive, located within the distal end of said tubular membrane and sealing to the distal end of said tubular membrane, and located distal to said colorimetric dye means.

13. A sensor according to claim 12 wherein said adhesive plus is white in color and spaced from the distal end of said fiber optic means no more than about 0.004".

14. A sensor according to claim 12 or claim 13 wherein said plug of adhesive comprises an epoxy based adhesive.

* * * * *